United States Patent [19]

Powell, Jr.

[11] Patent Number: 5,531,963
[45] Date of Patent: Jul. 2, 1996

[54] METHOD FOR DISINFECTING A CONTACT LENS AND DETECTING THE PRESENCE OF AN OXIDATIVE DISINFECTANT

[75] Inventor: Charles H. Powell, Jr., Irvine, Calif.

[73] Assignee: Allergan, Inc., Irvine, Calif.

[21] Appl. No.: 782,899

[22] Filed: Oct. 24, 1991

Related U.S. Application Data

[63] Continuation of Ser. No. 588,086, Sep. 25, 1990, abandoned.

[51] Int. Cl.⁶ .................................................. A61L 2/16
[52] U.S. Cl. ............................ 422/30; 422/28; 514/840
[58] Field of Search ........................... 422/28, 30, 300, 422/119; 252/106; 424/616; 514/839, 840; 134/901

[56] References Cited

U.S. PATENT DOCUMENTS

| Re. 32,672 | 5/1988 | Huth et al. .................... | 252/95 |
|---|---|---|---|
| 3,183,173 | 5/1965 | Oakes ........................... | 435/10 |
| 3,694,384 | 9/1972 | Factor et al. .................. | 521/25 |
| 3,910,296 | 10/1975 | Karageozian et al. ......... | 134/2 |
| 4,283,491 | 8/1981 | Dappen ......................... | 435/10 |
| 4,295,851 | 10/1981 | Neumann et al. .............. | 8/524 |
| 4,312,833 | 1/1982 | Clough et al. ................. | 422/30 |
| 4,521,375 | 6/1985 | Houlsby ......................... | 422/29 |
| 4,568,517 | 2/1986 | Kaspar et al. .................. | 422/30 |
| 4,585,488 | 4/1986 | Giefer ............................ | 252/106 |
| 4,655,957 | 4/1987 | Chromecek et al. .......... | 252/106 |
| 4,826,658 | 5/1989 | Kay ................................ | 422/30 |
| 4,851,353 | 6/1989 | Miike et al. .................... | 436/71 |
| 4,863,627 | 9/1989 | Davies et al. .................. | 422/28 |
| 4,976,921 | 12/1990 | Itagaki et al. .................. | 422/30 |
| 5,011,661 | 4/1991 | Schäfer et al. ................. | 422/30 |

FOREIGN PATENT DOCUMENTS

| 0110609 | 6/1984 | European Pat. Off. . | |
|---|---|---|---|
| 142623 | 5/1985 | European Pat. Off. . | |
| 0175801 | 4/1986 | European Pat. Off. . | |
| 0458578 | 11/1991 | European Pat. Off. . | |
| 2395034 | 1/1979 | France . | |
| 2003033 | 3/1979 | United Kingdom . | |
| 2220763 | 1/1990 | United Kingdom ............. | 206/5.1 |
| WO86/05695 | 10/1986 | WIPO . | |

OTHER PUBLICATIONS

The Encyclopedia of Chemistry, Third Edition, "Porphrins", pp. 910–912, Hampel et al.
The Encyclopedia of Chemistry, Third Edition, "Phthalocyanine Compounds", pp. 852–854, Hampel et al.
The Enzymes, vol. XII, Oxidation–Reduction, Part B, Electron Transfer (II) Oxygenases, Oxidases (I), Third Edition, pp. 557–567, Paul D. Boyer.
Sheu et al, "Iron–Hydroperoxide–Induced Phenylselenization of Hydrocarbons (Fenton Chemistry)", American Chemical Society 1989.
Alexandratos et al, "Dual Mechanism Bifunctional Polymers: Polystyrene–Based Ion–Exchange/Redox Resins", American Chemical Society 1986.
Mazur et al, "Integration of Fundamental Polymer Science and Technology".
Sheu et al, "Iron–Induced Activation of Hydrogen Peroxide for the Direct Ketonization of Methylenic Carbon [c–$C_6H_{12}$ c–$C_6H_{10}$(0)] and the Dioxygenation of Acetylenes and Arylolefins", American Chemical Society 1990.
Alexandratos et al, "Synthesis and Characterization of Bifunctional Ion–Exchange/Coordination Resins", Macromolecules 1987, 20, 1191–1196.

Primary Examiner—Robert J. Warden
Assistant Examiner—Theresa T. Snider
Attorney, Agent, or Firm—Frank J. Uxa

[57] ABSTRACT

An apparatus and method useful for disinfecting a contact lens are disclosed. The apparatus includes a color indicator element comprising an iodine component substantially irreversibly bonded to a solid material, preferably an anion exchange resin. The color indicator element is located in an oxidative disinfectant-containing liquid medium. This color indicator element provides a color indication of the presence of the oxidative disinfectant, e.g., hydrogen peroxide, in the liquid medium, and preferably a different color indication of the substantial absence of the oxidative disinfectant in the liquid medium.

17 Claims, 1 Drawing Sheet

METHOD FOR DISINFECTING A CONTACT LENS AND DETECTING THE PRESENCE OF AN OXIDATIVE DISINFECTANT

This application is a continuation of application Ser. No. 588,086, filed Sep. 25, 1990, now abandoned.

BACKGROUND OF THE INVENTION

The present invention relates to an apparatus and method useful for disinfecting a contact lens. More particularly, this invention relates to such an apparatus and method in which the presence of, and preferably the substantial absence of, an oxidative disinfectant is indicated.

Contact lenses should be periodically disinfected by the user to prevent infection or other deleterious effects on ocular health which may be associated with contact lens wear. Currently, there are several different conventional systems and methods which enable the user to disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are oxidative disinfectant, in particular hydrogen peroxide, disinfection systems. Disinfecting hydrogen peroxide solutions are effective to kill the bacteria and fungi which may contaminate contact lenses. However, residual hydrogen peroxide on a disinfected contact lens may cause irritation, burning or other trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens.

In order to avoid trauma to the eye caused by the presence of oxidative disinfectant on or in the lens, it would be advantageous to have an indication of the presence of such oxidative disinfectant. Additionally, it would be advantageous to have an indication of the substantial absence of such oxidative disinfectant, e.g., so that one would know it was safe to place the disinfected lens into one's eye.

Iodide ion is known to react with hydrogen peroxide to form free iodine which has a distinctive color. See, for example, Oakes U.S. Pat. No. 3,183,173. However, iodine has a substantial affinity for many contact lens materials so that the presence of free iodine in the liquid medium containing the oxidative disinfectant is to be avoided to prevent degradation of the contact lens.

There continues to be a need for a contact lens care system which effectively disinfects a contact lens and provides an indication of the presence of the oxidative disinfectant so that the disinfected lens can be safely and comfortably worn.

SUMMARY OF THE INVENTION

A new apparatus and method for disinfecting, and preferably cleaning, contact lenses has been discovered. The present system provides a clear and positive indication of the presence of an oxidative disinfectant, in particular hydrogen peroxide, in the lens disinfecting medium. This indication warns the lens wearer not to place the lens directly from the oxidative disinfectant-containing medium into the eye. Importantly, the means by which this indication is given is safe, does not interfere with the disinfecting method and has no substantial detrimental effect on the lens being disinfected. In addition, the present indicator preferably can be used many times, thus providing a cost effective approach to increasing the safety of contact lens disinfection.

In one broad aspect, the present invention is directed to an apparatus useful for disinfecting a contact lens which comprises a cup means and a color indicator means. The cup means acts to hold a liquid medium containing an oxidative contact lens disinfectant, in particular hydrogen peroxide. The color indicator means is adapted to be located at least partially in this liquid medium in the cup, and acts to provide a color indication of the presence of the oxidative contact lens disinfectant in the liquid medium. The color indicator means comprises an iodine component bonded, preferably substantially irreversibly bonded at the conditions at which the apparatus is used, to a solid material, preferably an anion exchange resin.

In another broad aspect of the present invention, a method for disinfecting a contact lens is provided. This method comprises contacting a contact lens to be disinfected with a liquid medium containing an oxidative disinfectant, in particular hydrogen peroxide, at conditions to effectively disinfect the contact lens. This contacting occurs in the presence of a solid material, preferably an anion exchange resin, having bonded thereto an iodine component in an amount effective to provide a color indication of the presence of the oxidative disinfectant in the liquid medium.

DETAILED DESCRIPTION OF THE INVENTION

The present invention is of value where oxidative disinfectants, in particular hydrogen peroxide, are used to disinfect all types of lenses, e.g., contact lenses, which are benefited by periodical disinfecting. Such lenses, e.g., conventional contact lenses, in particular soft contact lenses, may be made of any suitable material or combination of materials and may have any suitable configuration not substantially deleteriously affected by such oxidative disinfectants.

Although any oxidative disinfectant which is able to effectively disinfect a contact lens and to oxidize the bonded iodine component of the present invention may be employed, the much preferred oxidative disinfectant is hydrogen peroxide, especially aqueous solutions including hydrogen peroxide.

The present lens disinfecting apparatus includes a cup means, preferably a substantially transparent cup means, and a color indicator means.

The cup means acts to hold a liquid medium containing an oxidative contact lens disinfectant. Such cup means may be made of any suitable material, such as, for example, glass, polymeric materials and the like, which are resistant to the action of the oxidative disinfectant and have no substantial detrimental effect on the lens being disinfected. Examples of useful materials of construction include polymethylmethacrylate, polysulfone, acrylonitrile-butadiene-styrene terpolymers, polyphenylene oxide and the like. Preferably, the cup means, or at least a portion thereof, is substantially transparent so that the color indication or indications of the present system can be easily visually monitored.

The present color indicator means is adapted to be located at least partially in the liquid medium in the cup means. The color indicator means acts to provide a color indication of the presence of the oxidative contact lens disinfectant in the liquid medium, and preferably a different color indication of the substantial absence of the oxidative disinfectant in the liquid medium. The color indicator means comprises an iodine component bonded to a solid material. As used herein, the term "bonded" means that the iodine component is physically and/or chemically and/or otherwise associated with and/or secured to the solid material. In one embodiment, the iodine component is bonded to the solid material by ionic chemical bonds. The iodine component is preferably bonded to the solid material so that such bonding is substantially irreversible at the conditions, e.g., contact lens disinfecting conditions', at which the present system is utilized. This substantially irreversible bonding holds the iodine component away from the contact lens being treated so as not to interfere with such lens.

The iodine component useful in the present invention may be selected from iodine materials which are capable of functioning as described herein. The iodine component preferably can exist in two (2) states, i.e., a reduced state and an oxidized state. Preferably, these two states of the iodine component are both anionic. The iodine component is preferably oxidizable, e.g., to its oxidized state, by the oxidative contact lens disinfectant.

In one particularly useful embodiment, the reduced state iodine component is iodide ion ($I^-$), and the oxidized state iodine component is $I_{3^-}$.

The reduced state iodide ion, $I^-$, is substantially colorless, while the oxidized state $I_3^-$ ion is yellow in color. Thus, when the present indicator means in a liquid medium is subjected to an oxidative contact lens disinfectant, particularly hydrogen peroxide, the iodine component is in the oxidized state, e.g., $I_3^-$, and a color indication, e.g., a yellow color, is provided to indicate the presence of the oxidative disinfectant. When the oxidative disinfectant in the liquid medium is destroyed, e.g., reduced, and the oxidized state iodine component is preferably reduced to the reduced state iodine component, e.g., $I^-$, the color of the color indicator means changes, e.g., to colorless, providing a second color indication of the substantial absence of the oxidative disinfectant in the liquid medium. Such second color indication is preferably provided while the lens is in the liquid medium.

The amount of iodine component present in the color indicator means is such that the desired color indication or indications can be provided, and preferably visually recognized or monitored.

Any solid material which is suitable for bonding with the iodine component and which does not substantially interfere with the contact lens being treated or with the treatment method can be employed as a substrate for the iodine component. Preferably, such solid material is such as to allow for visual recognition of the color indication or indications provided. In certain instances, the solid material may have a color, or may include one or more other components which have a color, which interacts with the color, e.g., yellow, of the oxidized and/or reduced iodine component to provide a different color, e.g., different from yellow, to indicate the presence and/or substantial absence of the oxidative contact lens disinfectant. Such different color or colors are within the scope of the present invention.

In one particularly useful embodiment, the solid material comprises an anion exchange resin. Such resins are especially useful when the iodine component is anionic in character, e.g., $I^-$, $I_3^-$ and the like. Any anion exchange resin capable of bonding to iodide ions, and which does not substantially interfere with the contact lens being treated or the treatment method, can be employed. Examples of suitable anion exchange resins include polymers, such as styrene-divinylbenzene copolymers, hydroxyethyl methacrylate polymers and the like, which include quaternary ammonium moieties, such as tetraalkyl ammonium, e.g., trimethylethyl ammonium, dimethyl ethanol benzyl ammonium, trimethylbenzyl ammonium and the like. The use of anion exchange resins is particularly adapted to bonding the iodine component so that the bonding is substantially irreversible at the conditions at which the color indicator means is used.

The iodine component can be bonded to the solid material in any suitable manner, many of which are conventional and well known in the art. Soaking or impregnating the solid material with the iodine component, e.g., an aqueous solution of potassium iodide or the like may be employed. Conventional ion exchange techniques can be employed if the iodine component is to be bonded to an anion exchange resin.

The color indicator means, in use, is located in the liquid medium employed to disinfect a contact lens. Thus, the color indicator means can be secured in the inside, i.e., the interior space of the cup means where the liquid medium is held, of the cup means, may be adapted to move freely within the liquid medium in the cup means, or may be an integral part of the cup means.

For example, in the event, the color indication means is secured in the inside of the cup means, it can comprise a band or other piece of material adhesively or otherwise secured to the cup means. The color indicator means may be separate and apart from the cup means, such as in the form of a single disc or tablet, or a plurality of particles. In one embodiment, when the color indicator means is in the form of small particles, a retainer means, e.g., a screen element, can be provided in the cup means to keep the particles in place, and at the same time, allow the liquid medium in the cup means to freely contact the particles.

The color indicator means may be integral with the cup means. That is, for example, the cup means can be made at least in part from the material used as the color indicator means. In one particularly useful embodiment, the material used to make the cup means and the substrate material, e.g., the anion exchange resin, of the color indicator means are physically mixed together and processed, e.g., molded, to form the cup means, which is then further processed to bond the iodine component to the substrate within the cup means.

The present apparatus preferably further includes a basket means acting to hold a contact lens in the liquid medium in the cup means. The color indicator means can be secured to the basket means or can be an integral part of the basket means. The basket means can be made of the same or different material or materials relative to the material or materials used to make the cup means. Preferably, the lens means is substantially opaque, rather than transparent.

The cup means may have a removable cover, which may be made of the same or different material or materials used to make the cup means and which need not be transparent.

The liquid medium used in disinfecting a contact lens in the present invention preferably includes a disinfecting amount of oxidative disinfectant, in particular hydrogen peroxide. Preferably, a disinfecting amount of oxidative disinfectant means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Aqueous hydrogen peroxide solutions, preferably containing about 0.2% or about 0.5% to about 6% of hydrogen peroxide (w/v), are known to be effective disinfecting solutions for contact lenses. These solutions are effective at killing bacteria and fungi which may be found on contact lenses. Typically, the amount of hydrogen peroxide used in the liquid medium is well in excess of that required to effectively disinfect a contact lens. Substantial excess hydrogen peroxide is used so that the lens disinfection can be completed in a reasonable period to time.

The liquid medium used is selected to have no substantial detrimental effect on the lens being treated and to allow, and preferably to even facilitate, the present lens treatment or treatments. The liquid medium is preferably aqueous-based. A particularly useful liquid aqueous medium is that derived from saline, e.g., a conventional saline solution. During the disinfecting contacting, it is preferred that the liquid aqueous medium have a pH of less than about 8, more preferably in the range of about 3 to about 7.5 and still, more preferably about 6 to about 7.5. The liquid medium, e.g., aqueous liquid medium, preferably includes a buffer which is present in an amount effective to maintain the pH of the liquid medium in the desired range. This buffer may be present in the liquid medium and/or may be introduced into the liquid medium. Among the suitable buffers or buffering agents which may be employed are those which are conventionally used in contact lens care products. Examples of useful buffers include those with carbonate functionalities, bicarbonate functionalities, phosphate functionalities, borate functionalities, and the like and mixtures thereof. The buffers may be alkali metal and alkaline earth metal salts, in particular sodium and potassium.

The present color indicator means preferably provides enhanced antimicrobial activity when used in combination with hydrogen peroxide, in particular relatively low concentrations of hydrogen peroxide in aqueous solutions, such as about 0.2% to about 1% or about 3% of hydrogen peroxide (w/v). Thus, in one embodiment, not only does the color indicator means provide a color indication of the presence of hydrogen peroxide, and preferably a second, different color indication of the substantial absence of hydrogen peroxide, such color indicator means also enhances the antimicrobial activity of hydrogen peroxide, e.g., relative to a substantially similar contact lens disinfection system without the color indicator means. With the color indicator means present, a reduced concentration of hydrogen peroxide may be effective to disinfect contact lens. Such reduced hydrogen peroxide concentrations are beneficial since, for example, less residual hydrogen peroxide remains after lens disinfection so that there is less chance of eye irritation and other eye trauma caused by hydrogen peroxide remaining on the disinfected lens.

The use of an iodine component, e.g., in solution or preferably bonded to a solid material, to enhance the antimicrobial activity of hydrogen peroxide in a contact lens disinfecting system independent of the color indicating function described herein is included within the scope of the present invention. The iodine component is present in an amount effective to enhance the antimicrobial activity of the hydrogen peroxide-containing composition.

In one embodiment, an oxidative disinfectant destroying component, hereinafter referred to as an ODDC, is included in a solid composition, e.g., a tablet, capsule, one or more solid particles and the like, which is preferably introduced into the liquid medium about the same time as the lens to be disinfected is introduced into the liquid medium. Such solid compositions include one or more ODDCs in an amount effective to destroy all the residual oxidative disinfectant remaining in the liquid medium after the lens has been disinfected and preferably reduce the iodine component of the color indicator system to the reduced state.

Thus, such preferred solid compositions, which are preferably initially contacted with the oxidative disinfectant-containing liquid medium at substantially the same time as is the lens to be disinfected, allow for effective lens disinfection and, in addition, effectively destroy the residual oxidative disinfectant remaining in the oxidative disinfectant-containing liquid medium so that the disinfected lens can be removed from the liquid medium and placed directly into the eye for safe and comfortable wear. If, as is preferred, such compositions also reduce the iodine component of the color indicator means to the reduced state, a second color indication of the substantial absence of the oxidative disinfectant is provided, thus giving added assurance to the lens wearer that it is safe to wear the disinfected lens. Such preferred compositions may be present in the form of at least one item, e.g., tablet, capsule, one or more solid particles and the like, which includes a coated portion, e.g., a core such as a core tablet, and a barrier component. The coated portion includes the ODDC or ODDCs. The barrier component acts to delay the release of the ODDC or ODDCs from the coated portion into the liquid medium for a period of time, preferably sufficient to allow the lens to be disinfected. Preferably, the barrier coating substantially surrounds the coated portion.

Any suitable ODDC may be employed provided such ODDC has no substantial detrimental effect on the present system, on the disinfected lens or on the wearer of the disinfected lens. Among the useful ODDC are oxidative disinfectant reducing agents, peroxidases (meaning to include therein catalase) and mixtures thereof. In the event that one or more peroxidases are employed as the primary ODDC, i.e., the ODDC which acts to destroy the major portion of the residual oxidative disinfectant in the liquid medium, and it is desired to provide a second color indication of the substantial absence of the oxidative disinfectant in the liquid medium, one or more oxidative disinfectant reducing agents, particularly selected from those which reduce the oxidative disinfectant in preference to, i.e., at a faster rate than, the iodine component of the color indicator means, are preferably employed in combination with the one or more peroxidases. In the event that one or more oxidative disinfectant reducing agents are employed as the primary ODDC, and it is desired to provide a second color indication of the substantial absence of the oxidative disinfectant in the liquid medium, the reducing agent or agents are preferably selected from those which reduce the oxidative disinfectant in preference to the iodine component of the color indicator means. Using reducing agents which preferentially reduce the oxidative disinfectant provides added assurance that the oxidative disinfectant is substantially totally destroyed before a true second color indication of the substantial absence of the oxidative disinfectant is given.

Examples of the oxidative disinfectant reducing agents which are useful in the present invention are alkali metal in particular sodium, thiosulfates; thiourea; alkali metal, in particular sodium, sulfites; thioglycerol; alkali metal, in particular sodium, formates; pyruvic acid and salts of pyruvic acid; N-acetylcysteine; ene-diol compounds, e.g., ascorbic acid compounds, reductive acid compounds, isoascorbic acid compounds, glyoxylic acid compounds, squaric acid compounds, dihydroxymaleic acid compounds, dihydroxyfumaric acid compounds, and mixtures thereof. Typical examples of the foregoing ene-diol compounds are the acids themselves, e.g., ascorbic acid, ophthalmically acceptable salts of such acids, e.g., sodium ascorbate, ophthalmically acceptable esters of such acids, e.g., ascorbyl palmitate and any other ophthalmically acceptable derivatives of such acids, e.g., that retain the ene-diol molecular structure, mixtures thereof and the like. A particularly useful peroxidase is catalase. The peroxidases, and especially catalase, are very beneficial in the present invention since such ODDCs are effective to substantially eliminate hydrogen peroxide from a liquid medium in a reasonable period of time, e.g., on the order of about 1 minute to about 12 hours, preferably about 5 minutes to about 1 hour, after the ODDC is initially released into the liquid medium. Among the oxidative disinfectant reducing agents which preferentially reduce the oxidative disinfectant are pyruvic acid and salts of pyruvic acid, and controlled amounts of N-acetylcysteine and ene-diol compounds, in particular ascorbic acid compounds. Thus, such reducing agents can be used above or in conjunction with one or more other ODDCs, e.g., one or more peroxidases, to substantially completely destroy the oxidative disinfectant and provide a second color indication of the substantial absence of the oxidative disinfectant in the liquid medium.

The amount of ODDC employed is preferably sufficient to destroy all the oxidative disinfectant present in the liquid medium into which the ODDC is placed, and preferably to reduce the iodine component of the color indicator means to the reduced state. Excess ODDC may be employed. Very large excesses of ODDC are to be avoided since the ODDC itself may cause problems with the disinfected lens and/or the ability to safely and comfortably wear such disinfected lens. When catalase is employed a part of the ODDC, it is preferably present in an amount of about 100 to about 1000, more preferably about 150 to about 700 units of catalase activity per milliliter of liquid medium. For example, an especially useful amount of catalase for use in an aqueous solution containing about 3% (w/v) hydrogen peroxide is about 520 units of catalase activity/ml of solution.

The preferred delayed release of the ODDC or ODDCs into the liquid medium may be accomplished in any one of many suitable ways, a number of which are conventional and well known in the art. For example, the barrier component, e.g., coating, may be provided by coating a core tablet, or other particle, containing the ODDC or ODDCs with a slow dissolving coating material, which may ultimately be completely or only partially soluble in the liquid medium, or by including the ODDC or ODDCs in a matrix from which it may be slowly leached. Also, the matrix may be coated with a slow dissolving material so that the start of the slow release is delayed. The delayed release form of the ODDC or ODDCs is preferably such that substantially no release occurs during a delay period followed by rapid and substantially complete release of the ODDC or ODDCs at the end of the delay period. Such a result may be obtained by coating the ODDC or ODDCs with a slow dissolving coating.

Barrier components suitable as either coatings or as matrices, include water soluble vinyl polymers, such as polyvinylpyrrolidone, polyvinylalcohol and polyethyleneglycol; water soluble proteins; polysaccharide and cellulose derivatives, such as methyl cellulose, hydroxypropylmethyl cellulose, sodium carboxymethylcellulose; alginic acid and its salts and other derivatives; and the like and mixtures thereof. Mixtures of the above materials may be used.

The amount of barrier component used is not critical in the present invention provided that such barrier component functions as described herein. The barrier component or components may suitably be present in the range of about 1% to about 20% or more, based on the weight of the ODDC or ODDCs.

The solid compositions may be produced using any one of many suitable methods, a number of which are conventional and well known in the art.

The solid compositions may include other components, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here.

In a particularly useful embodiment, the contact lens may be subjected to the action of at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et. al. U.S. Pat. No. Re. 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof.

Preferred proteolytic enzymes are those which are substantially free of sulfhydryl groups or disulfide bonds, whose presence may react with the active oxygen of the disinfectant to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Keay, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two subclasses, subtilisin A and subtilisin B. In the subtilisin A grouping are enzymes derived from such species are *B. subtilis, B. licheniformis* and *B. pumilis*. Organisms in this sub-class produce little or no neutral protease or amylase. The subtilisin B sub-class is made up of enzymes from such organisms a *B. subtilis, B. subtilis* var. *amylosachariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

If such an enzyme or enzymes are employed, an effective amount is preferably used. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

Solid compositions which include such lens cleaning enzymes may be structured to release the enzyme, into the liquid medium which contacts the composition, at any time relative to the other component or components of the composition provided that the released enzyme is effective at the conditions present in the liquid medium to perform the cleaning function, as described herein. In one particularly useful embodiment, the cleaning enzyme is released into the liquid medium substantially immediately upon introducing the solid composition into the liquid medium.

In the event that a debris removing enzyme is present, the contact lens in the liquid medium is effectively cleaned of such debris. This cleaning action can occur before the lens is disinfected, at the time the lens is being disinfected, or after the lens is disinfected.

The disinfecting contacting preferably occurs at a temperature to maintain the liquid medium substantially liquid. It is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to substantially completely disinfect the lens being treated. Such contacting times can be in the range of about 1 minute to about 12 hours or more.

After such contacting, the liquid medium preferably includes substantially no residual, oxidative disinfectant and the disinfected lens can be removed from this liquid medium and placed directly into the eye for safe and comfortable wear. However, if the liquid medium includes one or more "cleaning" enzymes, it is preferred to rinse the disinfected lens, e.g., with saline, to free the lens of such enzyme prior to placing the disinfected lens into the eye.

DETAILED DESCRIPTION OF THE DRAWINGS

Figure 1:
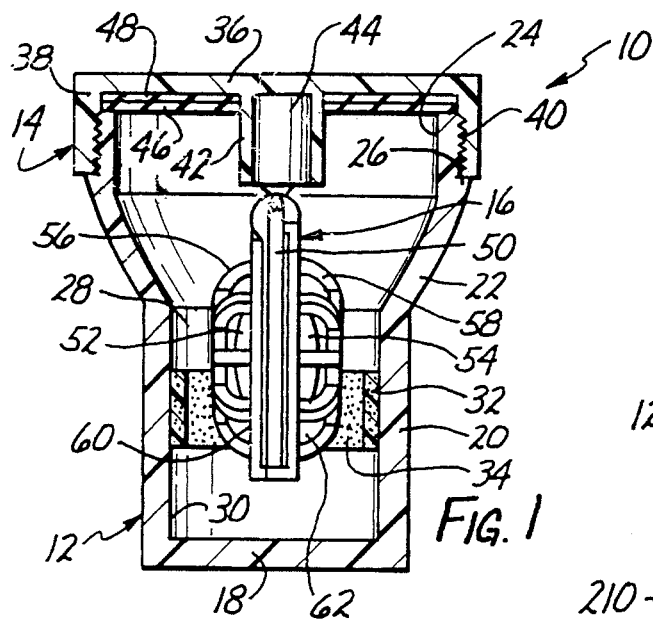
FIG. 1 is a front elevation view, partly in cross-section, illustrating one embodiment of the present apparatus.

Referring now to FIG. 1, a lens disinfection apparatus, shown generally at 10, include a lens container 12, a cover 14, and a lens basket 16.

Lens container 12 is made of a transparent, thermoplastic polymeric material, such as polymethylmethacrylate, and is made, e.g., molded using conventional techniques, as a single unit. Lens container 12 includes a bottom wall 18 and a sidewall 20. The upper portion 22 of sidewall 20 is flared outwardly. The top 24 of sidewall 20 includes a threaded outer surface 26. The cross-section of lens container 12 parallel to bottom wall 18 is generally circular. Lens container 12 defines an interior space 28 in which is placed a hydrogen peroxide-containing aqueous liquid medium.

Within interior space 28 and secured to the inner surface 30 of sidewall 20 is a color indicator band 32, which is an iodine component-containing anion exchange resin, e.g., a commercially available styrene divinylbenzene copolymer including covalently bonded trimethylethyl ammonium groups. This iodine component-containing anion exchange resin can be prepared using a starting anion exchange resin which includes sulfonate groups. This starting material is soaked in a potassium iodide solution so that iodide ions replace, or are exchanged for, the sulfonate groups on the anion exchange resin. Sufficient iodide ion is included so that the entire color indicator band 32 has a yellow color in the presence of hydrogen peroxide. Preferably, substantially all of the exchangeable sulfonate groups on the starting anion exchange resin are replaced by iodide ions.

The color indicator band 32 is generally right circular cylindrical in configuration and defines a through space 34 through which liquid can freely flow. Band 32 can be adhesively secured to inner surface 30 and is conveniently placed in interior space 28 to be completely submerged in the hydrogen peroxide-containing aqueous liquid medium during contact lens disinfecting.

Cover 14 includes a top wall 36 and a downwardly depending sidewall 38. Cover 14 is made of a non-transparent, thermoplastic polymeric material, such as polythenylene oxide. Top wall 36 is generally circular and the cross-section of sidewall 38 parallel to top wall 36 is generally circular. Sidewall 38 includes a threaded inner surface 40 the threads of which matingly engage the threads of threaded outer surface 26 to secure cover 14 to lens container 12. Cover 14 also includes a central, circular hollow projection 42 which, extends downwardly into lens container 12 when cover 14 is secured to lens container 12. An attachment element 44 of lens basket 16 is secured, e.g., by adhesive, interference fitting and the like, in the hollow space defined by projection 42. In this manner, lens basket 16 is secured to cover 14. A pair of foamed polymeric sealing elements 46 and 48 are fitted on the underside of cover 14 around projection 42 and act to provide a substantially liquid tight seal when cover 14 is secured to lens container 12.

Lens basket 16 is made of a non-transparent, thermoplastic polymeric material, such as polythenylene oxide. Like lens container 12 and cover 14, lens basket 16 can be made, e.g., molded, using conventional techniques. As noted above, lens basket 16 includes attachment element 44 which is secured to cover 14. Extending downwardly from attachment element 44 is basket body 50 which includes left lens mount 52 and right lens mount 54. Basket body 50 includes a series of through holes (not shown) which allow liquid to freely pass through the basket body.

A left basket cover 56 and a right basket cover 58 are both hingedly secured to basket body 50 and are structured to be "snapped" closed around left lens mount 52 and right lens mount 54, respectively, as desired, to form a left lens compartment 60 and a right lens compartment 62, respectively. The basket covers 56 and 58 are made separately from the other components of the lens basket 16. Each of the basket covers 56 and 58 include a series of through holes which allow liquid to flow freely through. However, these through holes are sized so that the contact lenses in lens compartments 60 and 62 cannot be removed when the lens covers 56 and 58 are closed. Left basket cover 56 may be marked with a "L" to indicate that it is to be used with the left contact lens. Similarly, the right basket cover 58 may be marked with a "R" to indicate that it is to be used with the right contact lens.

Lens disinfection apparatus 10 may be used as follows. With cover 14 removed from lens container 12, the contact lenses to be disinfected are placed on the appropriate left and right lens mounts 52 and 54, respectively and the left and right basket covers 56 and 58 are snapped closed.

A quantity, e.g., about 10 ml, of a 3% (w/v) hydrogen peroxide aqueous solution is placed in the interior space 28 of lens container 12 and completely immerses band 32. Prior to this solution being added, band 32 is white. Shortly after the hydrogen peroxide solution is added, the band 32 turns yellow in color, indicating the presence of hydrogen peroxide in the interior space 28. Cover 14 is applied to lens container 12 and secured in place. The contact lenses in lens compartments 60 and 62 are completely submerged in the hydrogen peroxide solution. Over a period of time, e.g., on the order of about 4 hours, the contact lenses are effectively disinfected. However, the band 32 remains yellow indicating the continued presence of hydrogen peroxide.

At this point, the cover 14 is removed from the lens container 12 and a tablet containing sufficient catalase to destroy the remaining hydrogen peroxide in the solution and sufficient sodium pyruvate reducing agent to provide the iodine component in the band 32 in a reduced state is added to the solution and the cover 14 is again secured to the lens container 12.

After another period of time, e.g., about one (1) hour, the band 32 is again colorless, indicating that the solution in interior space 28 contains substantially no hydrogen peroxide. The contact lens can then be removed from the lens compartments 60 and 62, rinsed with saline solution, and placed directly into the wearer's eyes for safe and comfortable wear.

Several alternative approaches to disinfecting, and cleaning, contact lenses using apparatus 10 are possible. For example, the catalase/sodium pyruvate combination with a delayed release coating can be added to the hydrogen peroxide-containing solution at substantially the same time the contact lenses are first contacted with this solution. The band 32 turns yellow indicating the presence of hydrogen peroxide. After a period of time, the delayed release coating dissolves releasing the catalase/sodium pyruvate combination into the solution. After another period of time, the band 32 is colorless, indicating that the solution in interior space 28 includes substantially no hydrogen peroxide. The disinfected contact lenses can be rinsed with saline solution and placed in the wearer's eyes for safe and comfortable wear.

Another alternative involves coating the delayed release coating with a hydrogen peroxide active enzyme, e.g., subtilisin A enzyme, in an amount effective to remove at least one type of debris, e.g., proteinaceous debris. In this embodiment, the enzyme/catalase/sodium pyruvate combination with the delayed release coating can be added to the hydrogen peroxide-containing solution at substantially the same time the contact lenses are first contacted with this solution. The band 32 turns yellow indicating the presence of hydrogen peroxide. After a period of time, during which the hydrogen peroxide-active enzyme removes proteinaceous debris from the contact lenses and the contact lenses are effectively disinfected, the delayed release coating releases the catalase and sodium pyruvate into the solution. After another period of time, the band 32 is colorless, indicating that the solution in interior space 28 includes substantially no hydrogen peroxide. The cleaned and disinfected contact lenses can be rinsed with saline solution to remove the subtilisin A enzyme and placed in the wearer's eyes for safe and comfortable wear.

Figure 2:
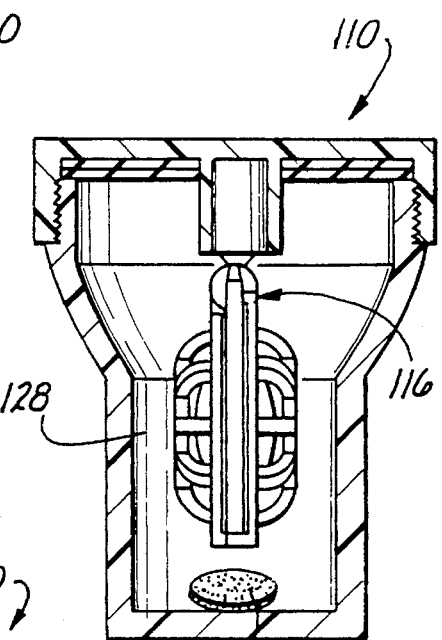
FIG. 2 is a front elevation view, partly in cross-section, illustrating another embodiment of the present apparatus.

FIG. 2 illustrates another embodiment of the present invention. Except as expressly stated elsewhere herein, this lens disinfection apparatus, shown generally at 110, is constructed and functions in a manner similar to lens disinfection apparatus 10. Components of apparatus 110 which correspond to components of apparatus 10 are indicated by corresponding reference numerals increased by 100.

One primary difference between apparatus 110 and apparatus 10 is that apparatus 110 does not include a color indicator band, such as color indicator band 32. Instead apparatus 110 includes a color indicator disc 70, which is made of an iodine component containing anion exchange resin, such as is color indicator band 32. Color indicator disc 70 is included in the interior space 128 of apparatus 110 during the time the contact lenses in lens basket 116 are being disinfected or cleaned and disinfected.

Color indicator disc 70 turns yellow in color, indicating the presence of hydrogen peroxide, and is colorless, indicating the substantial absence of hydrogen peroxide.

Figure 3:
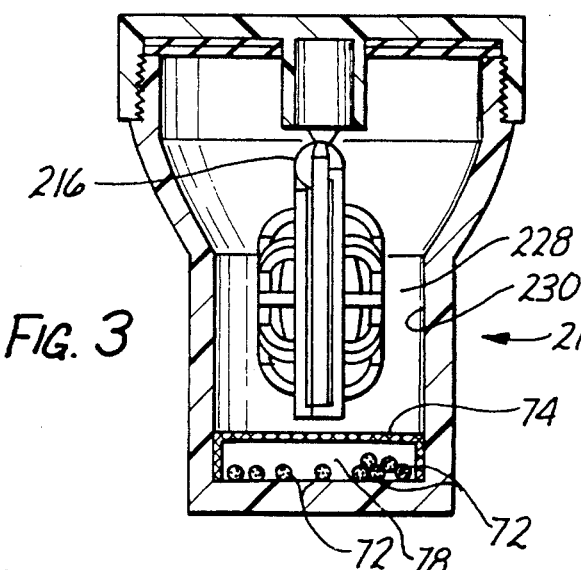
FIG. 3 is a front elevation view, partly in cross-section, illustrating an additional embodiment of the present apparatus.

FIG. 3 illustrates an additional embodiment of the present invention. Except as expressly stated elsewhere herein, this lens disinfection apparatus, shown generally at 210, is constructed and functions in a manner similar to lens disinfection apparatus 10. Components of apparatus 210 which correspond to components of apparatus 10 are indicated by corresponding reference numerals increased by 200.

One primary difference between apparatus 210 and apparatus 10 is that apparatus 210 does not include a color indicator band, such as color indicator band 32. Instead, apparatus 210 includes a plurality of color indicator beads 72 which are located at or near the bottom of interior space 228. A screen insert 74 is fitted within the inner wall 230 of lens container 212. Screen element 74 includes a plurality of holes sized so as to allow free access of the liquid material inside inner space 228 across screen element 74. At the same time, these holes are insufficiently large to allow the color indicator beads 72 to escape the compartment 78 defined by screen element 74 and the bottom portion of lens container 212.

Color indicator beads 72 are made of an iodine component containing anion exchange resin, such as color indicator band 32. Color indicator beads 72 are included in the space 78 defined by screen element 74 and the bottom portion of lens container 212 during the time the contact lenses are being disinfected or cleaned and disinfected. Color indicator beads 72 turn yellow in color, indicating the presence of hydrogen peroxide, and are colorless, indicating the substantial absence of hydrogen peroxide.

If desired, the screen element 74 can be removed from lens container 212 to replace color indicator beads 72. One important advantage of lens disinfection apparatus 210, for example relative to lens disinfection apparatus 110, is that the color indicator beads 72 remain in place between uses of apparatus 210 and are, therefore, not prone to being lost. The color indicator disc 70 of lens disinfection apparatus 110 can be removed between uses and become lost.

Figure 4:
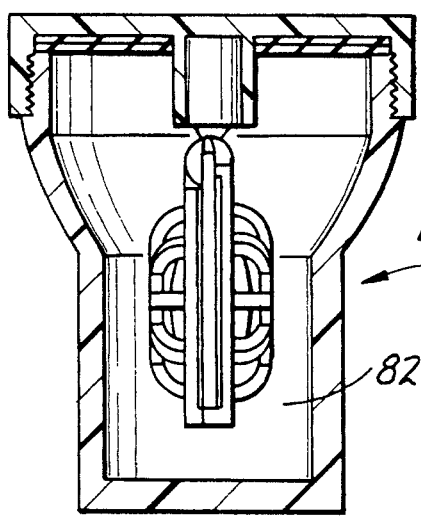
FIG. 4 is a front elevation view, partly in cross-section, illustrating a further embodiment of the present apparatus.

FIG. 4 illustrates a further embodiment of the present invention. Except as expressly stated elsewhere herein, the lens disinfection apparatus, shown generally at 310, is constructed and functions in a manner similar to lens disinfection apparatus 10. Components of apparatus 310 which correspond to components of apparatus 10 are indicated by corresponding reference numerals increased by 300.

One primary difference between apparatus 310 and apparatus 10 is that apparatus 310 does not include a color indicator band, such as color indicator band 32. Instead, apparatus 310 is provided with a color indicating lens container 80 which is made of a physical mixture of polymethylmethacrylate and the anion exchange resin described previously with regard to apparatus 10. This physical mixture of polymers is combined and then used to fabricate lens container 80, which is transparent. After lens container 80 is produced, it is soaked in a potassium iodide solution so that iodide ions replace, or are exchanged for, the sulfonate groups on the anion exchange resin. Sufficient anion exchange resin and iodide ion are included so that the lens container has a yellow color in the presence of hydrogen peroxide.

Lens container 80 includes an interior space 82 in which is placed a hydrogen peroxide-containing aqueous liquid medium.

Lens container 80 is configured substantially similarly to lens container 12. Lens container 80 turns a yellowish color, indicating the presence of hydrogen peroxide in the aqueous liquid medium in interior space 82, and is colorless, indicating the substantial absence of hydrogen peroxide in such aqueous liquid medium.

Figure 5:
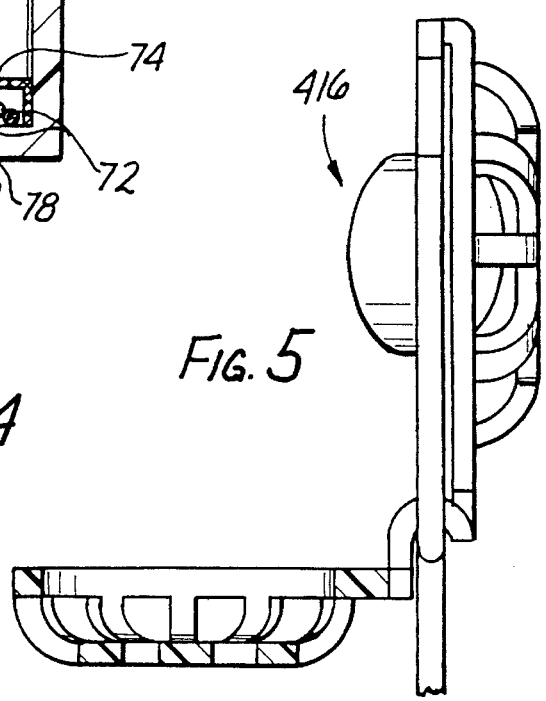
FIG. 5 is a front elevation view, partly in cross-section, illustrating another embodiment of the lens basket of the present apparatus.

FIG. 5 illustrates another embodiment of the lens basket of the present invention. Except as expressly stated elsewhere herein, this lens basket, shown generally at 416, is constructed and functions in a manner similar to lens basket 16. Components of lens basket 416 which correspond to components of lens basket 16 are indicated by corresponding reference numerals increased by 400.

One primary difference between lens basket 416 and lens basket 16 is the material of construction used in lens basket 416. Thus, lens basket 416 is made of a physical mixture of polythenylene oxide and an anion exchange resin, such as that described with regard to lens disinfection apparatus 10. After lens basket 16 is formed, it is soaked in a potassium iodide solution so that iodide ions replace, or are exchanged for, the sulfonate groups on the ion exchange resin. Sufficient anion exchange resin and iodide ion are included so that the entire lens basket 416 has a yellow color in the presence of hydrogen peroxide.

Lens basket 416 can be effectively utilized as both a lens basket and a color indicator for the presence of hydrogen peroxide. A particularly useful embodiment would involve replacing lens basket 116 with lens basket 416 in lens disinfection apparatus 110 and removing color indicator disc 70. In this embodiment, lens basket 416 turns yellow in color, indicating the presence of hydrogen peroxide, and is colorless, indicating the substantial absence of hydrogen peroxide.

The following non-limiting examples illustrate certain embodiments of the present invention.

EXAMPLE 1

A cartridge of anion exchange resin beads was selected for testing. The anion exchange resin was a styrene-divinylbenzene copolymer including tetraalkyl ammonium chloride moieties. The cartridge was sold by Alltech Associates, Inc. under the trademark Extract-Clean, and contained 0.35 g. of beads.

These beads were placed in a 25 ml beaker with 10 ml of a 3% (w/v) hydrogen peroxide aqueous solution. About 2 mg of potassium iodide crystals was added. A yellow color developed, which very quickly was absorbed by the beads, turning the white beads to a yellow color. The solution at this point was colorless. The addition of 1 ml of conventional starch indicator (1% by weight starch) produced no blue color in either the solution or the beads. That is, after the addition of the starch indicator, the solution remained colorless and the beads remained yellow.

A conventional catalase tablet was added to the hydrogen peroxide solution, and substantially all of the hydrogen peroxide was destroyed within 10 minutes of such addition. However, the yellow color remained in the beads. About 1 mg of N-acetylcysteine was added to the solution and the beads turned white in color within about 2 minutes after the reducing agent was dissolved in the solution.

The solution was poured off, leaving the beads in the beaker. A 10 ml portion of a 3% (w/v) hydrogen peroxide aqueous solution was added to the beaker. The beads turned yellow in color (to the previous color intensity) within about 2 minutes of such addition. A conventional catalase tablet was added to the solution. Before the hydrogen peroxide was completely destroyed, about 1 mg of N-acetylcysteine was added to the solution. The beads turned white in color about 1 minute after the hydrogen peroxide in the solution was substantially completely destroyed.

The above cycle was repeated 8 more times. The intensity of the yellow color remained substantially unchanged. Thus, at the conditions employed, the bonding of the iodine component onto the anion exchange resin beads was irreversible, while the color change of the beads is reversible and depends on the presence and substantial absence of hydrogen peroxide in the solution.

Thus, the use of an iodine component bonded to an anion exchange resin is a workable system for indicating the presence of hydrogen peroxide in a contact lens disinfection system. In addition, this system is also effective to provide a second color indication of the substantial absence of hydrogen peroxide where catalase is used to destroy the residual hydrogen peroxide, provided that a small amount of reducing agent is added to the solution to provide for the reduction of the iodine component.

EXAMPLE 2

The iodine component-containing beads of Example 1 were again combined with 10 ml of a 3% (w/v) hydrogen peroxide aqueous solution in a 25 ml beaker. A yellow color developed in the beads within about 30 seconds of such combination. An enzymatic cleaning tablet, sold by Allergan, Inc. under the trademark Ultrazyme® was added to the solution. This tablet included about 30 mg of N-acetylcysteine. The solution, including this tablet, had a pH in excess of 8. The yellow color of the beads disappeared within about 30 seconds from the tablet addition and did not return even after allowing the solution to stand overnight. The amount of N-acetylcysteine added to the solution was insufficient to destroy all the hydrogen peroxide in the solution, so that some hydrogen peroxide remained in the solution even though the beads were white in color.

These results indicate that N-acetylcysteine preferentially reduces the iodine component relative to hydrogen peroxide. Also, it is believed that the relatively high pH of the solution (in excess of about 8) contributed to the loss of the yellow color of the beads. Thus, when N-acetylcysteine is used as the sole hydrogen peroxide destroying component, particularly at a pH in excess of about 8, the iodine component/ anion exchange resin color indicator system is unreliable in providing a second signal of the substantial absence of hydrogen peroxide.

EXAMPLE 3

Example 2 is repeated except that sodium pyruvate instead of N-acetylcysteine is used and the pH of the solution is controlled, buffered, at about 7.4.

The yellow color of the beads remains after the sodium pyruvate is added, even after the solution is allowed to stand overnight.

An additional amount of sodium pyruvate is added to the solution. This additional amount is sufficient to reduce all the hydrogen peroxide remaining in the solution and to reduce the iodine component to a reduced state. Within about 1 hour after such additional addition, substantially all of the hydrogen peroxide in the solution is reduced (eliminated) and the beads are white in color.

These results indicate that sodium pyruvate preferentially reduces hydrogen peroxide relative to the iodine component in the beads. Thus, when this material is used as the sole hydrogen peroxide destroying component, the iodine component/anion exchange resin color indicator system is reliable in providing a second signal of the substantial absence of hydrogen peroxide.

EXAMPLE 4

This example illustrates a lens cleaning/disinfecting embodiment of the present invention, with specific reference to FIG. 3.

A pair of protein-based debris laden contact lenses are placed in lens basket 216. 10 ml of a saline solution containing 3% (w/v) of $H_2O_2$ and 0.3% by weight of boric acid is added to the interior space 228, and the lens basket 216 is positioned so that the contact lenses are completely submerged in the solution in lens container 212. The pH of this solution is about 7.5. At this point the beads 72, which are produced in a manner similar to the beads described in Example 1, turn yellow in color.

A layered, delayed release tablet is dropped into the solution in lens container 212. The center core of the tablet includes 1.5 mg of crystalline catalase and 0.5 mg of N-acetylcysteine. The outer layer of the tablet includes 0.4 mg of subtilisin A enzyme. A delayed release layer between the inner layer and the outer layer is structured and designed to dissolve sufficiently in two hours after being exposed to the solution in the lens container 212 to release the catalase and N-acetylcysteine into the solution.

Upon being dropped into the solution, the outer layer of the tablet dissolves to release the subtilisin A into the solution. The enzyme in the outer layer begins to attack and remove the protein-based debris on the lenses. Substantially all of the protein-based debris is removed from the lenses. In addition, the contact lenses are effectively disinfected. Thirty minutes after the layered tablet is first dropped into the solution, the catalase and N-acetylcysteine are released into the solution and destroy the residual hydrogen peroxide in the solution and reduce the iodine component in the beads 72 to a reduced state. At this point, the beads 72 turn white in color. Upon seeing the white beads 72, the lens wearer removes the cleaned/disinfected lenses from the solution, rinses them with physiological saline solution to remove the subtilisin A enzyme, and places them in his/her eyes. It is found that the contact lenses are effectively disinfected and cleaned of protein-based debris. The lens wearer experiences no discomfort or eye irritation from wearing the disinfected and cleaned contact lenses.

EXAMPLE 5

Example 4 is repeated except that the layered, delayed release tablet is replaced by a tablet including 0.4 mg of subtilisin A enzyme which is released immediately into the solution.

After six hours, the beads 72 are yellow in color and the contact lenses are effectively cleaned and disinfected. At this point, the solution is discarded and replaced by a physiological saline solution containing 0.3% by weight of sodium pyruvate. Within about one hour after this solution replacement, substantially all of the residual hydrogen peroxide on the cleaned/disinfected contact lenses and on the lens basket 216 and lens container 212 is reduced (eliminated) and the beads are white in color.

The cleaned/disinfected lenses are removed from this solution, rinsed with physiological saline solution to remove the remaining traces of the subtilisin A enzyme and placed in the wearer's eyes. It is found that the contact lenses are effectively disinfected and cleaned of protein-based debris. The lens wearer experiences no discomfort or eye irritation from wearing the disinfected and cleaned contact lenses.

EXAMPLE 6

Beads, about 5 g, of an anion exchange resin, sold by Aldrich Chemical Co., Inc. under the trademark Amberlite 940-IRA, were impregnated with 100 mg of potassium iodide. The bonding of the iodine component to the beads was substantially irreversible at the conditions at which the iodine component-containing beads were tested.

Using these iodine component-containing beads in 10 ml of a 0.5% (w/v) hydrogen peroxide aqueous solution, the kill rate of various microorganisms was determined. As control tests, the kill rates were determined without the beads. Results of these tests were as follows:

| Micro- organism | KILL RATE, log reductions | | | | | |
|---|---|---|---|---|---|---|
| | Iodine Component- Containing Beads | | | Control | | |
| | 30 min. | 1 hour | 2 hour | 30 min. | 1 hour | 2 hour |
| S. aureus | 2.60 | NR | NR | 0.60 | 1.60 | NR |

-continued

| Micro- | KILL RATE, log reductions | | | | | |
|---|---|---|---|---|---|---|
| | Iodine Component-Containing Beads | | | Control | | |
| organism | 30 min. | 1 hour | 2 hour | 30 min. | 1 hour | 2 hour |
| S. marcescens | 4.00 | NR | NR | 1.30 | 5.00 | NR |
| C. albicans | 1.12 | 1.60 | 5.00 | 0.70 | 1.12 | 3.60 |
| A. fumigatus | NK | NK | 0.12 | 0.05 | NK | 0.05 |

NK = No kill
NR = No recovery

These results indicate that the iodine component-containing beads do enhance the activity of the system against S.aureus and S. marcescens, but has little or no effect on the activity against C. albicans and A. fumigatus.

While this invention has been described with respect to various specific examples and embodiments, it is to be understood that the invention is not limited thereto and that it can be variously practiced within the scope of the following claims.

What is claimed is:

1. A method for disinfecting a contact lens comprising:

contacting a contact lens to be disinfected with a liquid medium containing an oxidative disinfectant at conditions to effectively disinfect said contact lens, thereby disinfecting said contact lens, said contacting occurring in the presence of a solid material which is and remains insoluble in said liquid medium throughout said method and which has bonded thereto an iodine component in an amount effective while bonded to said solid material to provide a color indication of the presence of said oxidative disinfectant in said liquid medium.

2. The method of claim 1 wherein said bonding of said iodine component to said solid material is irreversible at the conditions of said contacting.

3. The method of claim 1 wherein said oxidative disinfectant is hydrogen peroxide, and said liquid medium is an aqueous liquid medium having a pH of less than about 8.

4. The method of claim 1 wherein said solid material is an anion exchange resin.

5. The method of claim 1 wherein said iodine component is oxidized during said contacting.

6. The method of claim 1 which further comprises destroying said oxidative disinfectant so as to provide a substantially oxidative disinfectant-free liquid medium.

7. The method of claim 6 wherein said destroying step further acts to provide said iodine component while bonded to said solid material in a reduced state effective to provide a different color indication of the substantial absence of said oxidative disinfectant in said substantially oxidative disinfectant-free liquid medium.

8. The method of claim 7 wherein a reducing component is present during said destroying step in an amount effective to provide said iodine component in said reduced state.

9. The method of claim 8 wherein said reducing component is present during said destroying step in an amount effective to provide said substantially oxidative disinfectant-free liquid medium, said reducing component being selected from those which preferentially reduce said oxidative disinfectant relative to said iodine component.

10. The method of claim 9 wherein said oxidative disinfectant is hydrogen peroxide, and said liquid medium is an aqueous liquid medium and has a pH in the range of about 3 to about 7.5 during said contacting.

11. The method of claim 8 wherein a peroxidase component is present during said destroying step in an amount effective to provide said substantially oxidative disinfectant-free liquid medium.

12. The method of claim 11 wherein said oxidative disinfectant is hydrogen peroxide.

13. The method of claim 1 which further comprises contacting said contact lens with at least one enzyme capable of removing debris from a contact lens in an amount effective to substantially remove at least one type of debris from said contact lens.

14. A method for disinfecting a contact lens comprising:

contacting a contact lens to be disinfected with a liquid aqueous medium containing hydrogen peroxide and having a pH of less than about 8 at conditions to effectively disinfect said contact lens, thereby disinfecting said contact lens, said contacting occurring in the presence of an iodine component bonded, irreversibly at said contacting conditions, to a solid anion exchange resin which is and remains insoluble in said liquid aqueous medium throughout said method, said bonded iodine component being present in an amount to provide a first color indication of the presence of hydrogen peroxide in said aqueous liquid medium, said bonded iodine component being present in an oxidized state during said contacting; and, thereafter, contacting said liquid aqueous medium with a reducing component present in an amount effective to chemically reduce substantially all of the hydrogen peroxide in said liquid aqueous medium and chemically reduce said bonded oxidized iodine component so that a second color indication of the substantial absence of hydrogen peroxide in said liquid aqueous medium is provided, said reducing component being selected from those which preferentially chemically reduce hydrogen peroxide relative to said bonded oxidized iodine component.

15. A method for disinfecting a contact lens comprising:

contacting a contact lens to be disinfected with a liquid aqueous medium containing hydrogen peroxide and having a pH of less than about 8 at conditions to effectively disinfect said contact lens, thereby disinfecting said contact lens, said contacting occurring in the presence of an iodine component bonded, irreversibly at said contacting conditions, to a solid anion exchange resin which is and remains insoluble in said liquid aqueous medium throughout said method, said bonded iodine component being present in an amount to provide a first color indication of the presence of hydrogen peroxide in said aqueous liquid medium, said bonded iodine component being present in an oxidized state during said contacting; and, thereafter, contacting said liquid aqueous medium with a peroxidase component present in an amount effective to destroy substantially all of the hydrogen peroxide in said liquid aqueous medium and a reducing component present in an amount effective to chemically reduce said bonded oxidized iodine component so that a second color indication of the substantial absence of hydrogen peroxide in said liquid aqueous medium is provided.

16. A method for disinfecting a contact lens comprising:

contacting said contact lens to be disinfected with a liquid medium containing hydrogen peroxide at conditions to effectively disinfect said contact lens, thereby disinfecting said contact lens, said contacting occurring in the presence of a solid material which is and remains insoluble in said liquid medium throughout said method and to which is bonded an iodine component in an amount effective while bonded to said solid material to enhance the antimicrobial activity of said liquid medium.

17. The method of claim 16 wherein said solid material is an anion exchange resin, and said bonding of said iodine component to said solid material is irreversible at the conditions of said contacting.

* * * * *

UNITED STATES PATENT AND TRADEMARK OFFICE
CERTIFICATE OF CORRECTION

PATENT NO. : 5,531,963
DATED : July 2, 1996
INVENTOR(S) : Powell, Jr.

It is certified that error appears in the above-indentified patent and that said Letters Patent is hereby corrected as shown below:

Column 6, line 49; delete "are-preferably" and insert in place thereof --are preferably--.

Claim 2, line 37; add the word "substantially" before irreversible.

Claim 17, line 2; add the word "substantially" before irreversible.

Signed and Sealed this

Twentieth Day of October, 1998

Attest:

BRUCE LEHMAN

Attesting Officer

Commissioner of Patents and Trademarks